US006670335B2

(12) United States Patent
Singh et al.

(10) Patent No.: US 6,670,335 B2
(45) Date of Patent: Dec. 30, 2003

(54) FLUOROURACIL-CONTAINING FORMULATION

(75) Inventors: B. Sandhya Singh, San Jose, CA (US); Subhash J. Saxena, Belmont, CA (US)

(73) Assignee: A. P. Pharma, Inc., Redwood City, CA (US)

( * ) Notice: Subject to any disclaimer, the term of this patent is extended or adjusted under 35 U.S.C. 154(b) by 89 days.

(21) Appl. No.: 09/799,792

(22) Filed: Mar. 5, 2001

(65) Prior Publication Data

US 2002/0165198 A1 Nov. 7, 2002

(51) Int. Cl.⁷ .......................... A61K 31/70; A61K 31/50
(52) U.S. Cl. ......................................... 514/50; 514/256
(58) Field of Search ................... 514/256, 50

(56) References Cited

U.S. PATENT DOCUMENTS

| | | | |
|---|---|---|---|
| 4,690,825 A | 9/1987 | Won | 424/501 |
| 4,849,426 A | 7/1989 | Pearlman | 514/274 |
| 4,873,091 A | 10/1989 | Jankower et al. | 424/489 |
| 5,073,365 A | 12/1991 | Katz et al. | 424/489 |
| 5,135,740 A | 8/1992 | Katz et al. | 424/401 |
| 5,145,675 A | 9/1992 | Won | 424/78.31 |
| 5,627,187 A | 5/1997 | Katz | 514/274 |

FOREIGN PATENT DOCUMENTS

WO  WO 00/00159  1/2000

OTHER PUBLICATIONS

Physicians' Desk Reference, PDR 54 Edition 2000, pp. 497–498 and pp. 1394–1395.
Index from the US Product Drug Approvals for drugs beginning with the letter "F" from the FDA's web site, printed on Nov. 17, 2000, pp. 1, 7 & 8.
Jonathan K. Wilkin, NDA Approval Letter addressed to Dermik Laboratories, Inc. for (fluorouracil cream), approved on Oct. 27, 2000, 3 pages, with draft printed labeling.
Once–a–day Carac Fluorouracil cream 0.5%, Prescribing Information received from web address: http://www.dermik.com/prod/carac/pi.html, on Nov. 19, 2001.

*Primary Examiner*—Zohreh Fay
(74) *Attorney, Agent, or Firm*—Heller Ehrman White & McAuliffe LLP; Stephanie L. Seidman; Dale Roger

(57) ABSTRACT

Oil-in-water emulsion formulations contain both free fluorouracil and fluorouracil impregnated in porous microparticles. The formulations are suitable for topical administration, and are useful for the treatment of solar keratoses, actinic keratoses, and superficial basal cell carcinomas.

20 Claims, No Drawings

FLUOROURACIL-CONTAINING FORMULATION

BACKGROUND OF THE INVENTION

1. Field of The Invention

This invention relates to a formulation containing fluorouracil, and to its uses.

2. Description of Related Art

Fluorouracil (USP, INN), also known as 5-fluorouracil or 5-FU, chemically 5-fluoro-2,4(1H,3H)-pyrimidinedione, is a fluorinated nucleoside known to be useful as an antineoplastic antimetabolite. It effectively inhibits RNA function and thymidylate synthesis by blocking the methylation reaction of deoxyuridylic acid.

Fluorouracil delivered by injection has been reported to have beneficial effects in carcinomas of the breast and GI tract, of the ovary, cervix, urinary bladder, prostate, pancreas, and oropharyngeal areas. It appears to exhibit even greater efficacy when administered concomitantly with other agents, including cyclophosphamide, methotrexate, and cisplatin.

Fluorouracil delivered topically is widely used to treat actinic or solar keratoses and superficial basal cell carcinomas. Topical fluorouracil exists in solution formulations containing 1%, 2%, and 5% by weight fluorouracil, and cream formulations containing 1% and 5% by weight fluorouracil. See the *Physicians' Desk Reference.* 54 ed., Medical Economics Co., Montvale N.J., 2000, at pages 497–498 (Fluoroplex) and 1394–1395 (Efudex). The disclosures of these and other documents referred to elsewhere in this application are incorporated herein by reference. However, these formulations, while beneficial, are irritating to the skin, causing side effects such as burning, allergic contact dermatitis, erythema, pain, pruritus, and ulceration.

It would be of value to have a formulation containing fluorouracil, where a part of the fluorouracil is present impregnated in porous microparticles.

SUMMARY OF THE INVENTION

In a first aspect, this invention provides a formulation containing fluorouracil, comprising:
  (i) an oil-in-water emulsion; and
  (ii) dispersed within the oil-in-water emulsion,
    (a) fluorouracil; and
    (b) fluorouracil-impregnated porous microparticles.

In a second aspect, this invention provides a method of topical application of fluorouracil, comprising the topical administration of the formulation of the first aspect of this invention.

In a third aspect, this invention provides a method of treating a disease state capable of treatment by topical administration of fluorouracil, comprising the topical administration of the formulation of the first aspect of this invention.

DETAILED DESCRIPTION OF THE PREFERRED EMBODIMENTS

According to the this invention, there are obtained oil-in-water emulsion formulations containing fluorouracil, in which the fluorouracil is present both free and as fluorouracil-impregnated porous microparticles. Thus, the invention comprises formulations in which a part of the fluorouracil is present for immediate release upon topical application, and the remainder of the fluorouracil is present as a reservoir in porous microparticles. Formulations according to this invention are stable and topically acceptable, thereby providing attractive forms for the topical administration of fluorouracil; and are useful for disease states in which topical administration of fluorouracil is indicated, such as actinic or solar keratoses and superficial basal cell carcinomas. Furthermore, such formulations show equal efficacy to, but are less irritating than, other formulations currently on the market containing equivalent concentrations of fluorouracil.

A "therapeutically effective amount" means the amount that, when administered to an animal for treating a disease, is sufficient to effect treatment for that disease.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

Number ranges given in the specification, such as size ranges and the like, should be considered approximate, unless specifically stated.

Ingredient names are taken from the *International Cosmetic Ingredient Dictionary and Handbook,* 8th edition, 2000, Cosmetic, Toiletry, and Fragrance Association, Washington, DC.

The Porous Microparticles

Suitable porous microparticles for this invention are solid, water-insoluble, polymeric microparticles having a network of interconnected pores open to the particle surface, providing substantially full communication between the internal pore space and the particle exterior surface. Microparticles of this type, and methods for their preparation and impregnation, are disclosed in U.S. Pat. Nos. 4,690,825 (Won), 4,873,091 (Jankower et al.), 5,073,365 (Katz et al.), 5,135,740 (Katz et al.), and 5,145,675 (Won et al.).

The porous microparticles are generally spherical in shape and have a weight average diameter from less than 1 $\mu$m to about 500 $\mu$m or more, particularly from about 5 $\mu$m to about 100 $\mu$m, more particularly from about 10 $\mu$m to about 50 $\mu$m, especially about 20 $\mu$m. The pore dimensions within the microparticles may vary, with optimum dimensions depending on the polymers used to form the microparticles and the diffusive characteristics of the material to be impregnated. Typical pore volumes are from about 0.01 cm$^3$/g to about 4 cm$^3$/g, particularly from about 0.1 cm$^3$/g to about 2 cm$^3$/g; typical surface areas are from about 1 m$^2$/g to about 500 m$^2$/g, particularly from about 20m$^2$/g to about 350 m$^2$/g; and typical pore diameters are from about 0.0001 $\mu$m to about 3 $\mu$m, particularly from about 0.003 $\mu$m to about 1 $\mu$m. The average diameter of the microparticles may be determined by sedimentation or by a laser microsizer; the pore volume may be determined by mercury intrusion; and the surface area may be determined by nitrogen adsorption (the BET method).

The porous microparticles are composed of organic polymers and are formed by suspension polymerization of a mixture of monoethylenically unsaturated and polyethylenically unsaturated monomers in the presence of a porogen (a pore-forming agent), as described in the patents listed above. Monoethylenically unsaturated monomers suitable for forming microparticles for use in this invention include styrene, ethylvinylbenzene, vinyltoluene, acrylic acid and its esters, such as ethyl acrylate, methacrylic acid and its esters, such as methyl methacrylate and lauryl methacrylate, vinyl esters, such as vinyl acetate, vinyl propionate, vinyl stearate, and vinyl laurate, vinylic ketones, such as vinyl methyl ketone and methyl isopropenyl ketone, and vinyl ethers, such as vinyl methyl ether, and the like. Polyethylenically unsaturated monomers suitable for forming microparticles for use in this invention include divinylbenzene, divinyl ketone, divinyl sulfone, polyvinyl or polyallyl esters of dibasic or polybasic acids, such as divinyl sebacate, diallyl adipate, diallyl phthalate, diallyl sebacate, polyvinyl or polyallyl ethers of diols or polyols, such as ethylene glycol divinyl ether and diethylene glycol diallyl ether, polyacrylate or polymethacrylate esters of diols or polyols, such as ethylene glycol dimethacrylate, polyethylene glycol diacrylate, trimethylolpropane trimethacrylate, and the like. Typically the monoethylenically unsaturated monomer will be present at from 20% to 80% of the monomer mixture, with the polyethylenically unsaturated monomer forming the remainder of the mixture. Preferred monomer mixtures include styrene/divinylbenzene, vinyl stearate/divinylbenzene, methyl methacrylate/ethylene glycol dimethacrylate, and lauryl methacrylate/ethylene glycol dimethacrylate.

The mixture of monomers, together with the porogen, which is typically a moderately low-boiling hydrocarbon such as heptane or toluene, and a polymerization catalyst, such as a peroxide, are added to an aqueous phase, typically containing a dispersant, and stirred to form a suspension of the organic phase in the aqueous phase with droplets of the desired size of the resulting particles. On heating and continued stirring, the monomers polymerize to form solid porous microparticles having the pores filled with the porogen. The microparticles are filtered, washed with water to remove the dispersants and then with volatile organic solvents such as isopropanol to remove unreacted monomers and the porogen, and then dried under vacuum to afford the porous microparticles.

Microparticles of this type are commercially available from Enhanced Derm Technologies, Inc. under the trademark MICROSPONGE®.

The Fluorouracil-impregnated Porous Microparticles

Fluorouracil-impregnated porous microparticles suitable for use in this invention may be prepared by mixing the porous microparticles with a solution containing fluorouracil and subsequently removing the solvent. Typically, the fluorouracil-impregnated porous microparticles will have a fluorouracil content from about 1% to about 50%, particularly from about 5% to about 30%, more particularly from about 10% to about 20%, especially around 15% by weight, of the impregnated microparticles.

The fluorouracil may be entrapped in the microparticles as a fluorouracil blend containing additional ingredients, if so desired; and/or additional optional ingredients may be entrapped in the microparticles after entrapment of the fluorouracil. A typical optional additional ingredient in the microparticles is an emollient or skin conditioner, such as dimethicone. The amount of the emollient may vary and is not critical to this invention: in most applications, an amount ranging up to about 60% by weight of the impregnated microparticles is suitable.

Typically, the fluorouracil (fluorouracil blend) will be dissolved in water or a volatile organic solvent, such as a lower alcohol or lower ketone, for example isopropanol or acetone, and the solution mixed with the microparticles so that the solution is absorbed into the pores of the microparticles. Once the microparticles have absorbed the solution, the solvent is removed by evaporation, typically under reduced pressure and optionally with mild heating, avoiding excessive temperatures that may speed decomposition or oxidation of the fluorouracil. This impregnation process may occur in either a single step in multiple steps (as discussed in Example 1).

Oil-in Water Emulsions

The oil-in-water emulsions of the invention comprise lipophilic (oil) droplets in a continuous hydrophilic (water) phase. These emulsions may comprise some 10–40% oil phase and 60–90% water phase. The water phase may contain humectants, which prevent the desiccation and consequent hardening of the emulsions. Oil-in-water emulsions of the invention may typically contain, but are not limited to, polyoxyethylene alcohol (varying in the fatty alcohol and in the degree of polymerization of polyethylene glycol), aryl alcohol, wax, silicone oil, mineral oil, deionized water, glycerol, and additional emulsifying, thickening, and preservative agents. Emulsifiers constitute an important component of the formulations, as they lend to the stability of the emulsion as a whole by coating the oil droplets. Emulsifiers are, essentially, surfactants. These surfactants can be ionic or non-ionic, and they can be used alone or in admixture. They include cetearyl alcohol and sodium cetearyl sulfate, PEG-1000 monocetyl ether, or quaternary ammonium salts such as alkyl trimethyl ammonium bromide; likewise, the polyol ester glycerol monostearate and potassium stearate, sodium lauryl sulfate, and ethoxylated fatty alcohols constitute good co-emulsifiers. Fatty acids like stearic acids may be included to regulate the consistency of the emulsion. Finally, polymers such as carbomers can be included in small amounts to stabilize the emulsion.

The formulation of the invention contains both free fluorouracil, and fluorouracil-impregnated porous microparticles. Typically, the formulation will have a total fluorouracil content of at least 0.001%, particularly at least 0.1%, more particularly at least 0.5%; and not more than 10%, particularly not more than about 5% by weight of the formulation. Typical formulation strengths would be those already seen for topical fluorouracil solutions and creams of the prior art, such as 1%, 2%, and 5%; but strengths both above and below these are within this invention. Also, the formulation will typically have a free fluorouracil content of at least 0%, particularly at least 10%, more particularly at least 20%; and not more than 80%, particularly not more than 70%, more particularly not more than 50%, by weight of the total fluorouracil content. For a 5% fluorouracil formulation, a suitable free fluorouracil content is about 30% by weight of the total fluorouracil content, so that the formulation contains about 1.5% free fluorouracil and about 3.5% fluorouracil impregnated in porous microparticles; a 1% fluorouracil formulation might contain 0.3% free fluorouracil and 0.7% fluorouracil in porous microparticles. It is a particular advantage of the formulation of this invention that the fluorouracil is present in the formulation both free in the emulsion for immediate activity and as a reservoir impregnated in porous microparticles for release and activity over an additional period of time.

The formulation may also contain additional ingredients such as antioxidants, chelating agents, colorants, fragrances, preservatives, and the like, as necessary or desired, typically in amounts less than 2% by weight of the formulation, as well as suitable thickening agents. Both water-soluble and oil-soluble antioxidants may be used. Examples of water-soluble antioxidants include ascorbic acid and its salts, such as sodium ascorbate, isoascorbic acid and its salts, sodium sulfite, sodium metabisulfite, sodium thiosulfite, thiols such as thioglycerol, thiosorbitol, thiourea, thioglycolic acid, and cysteine, and the like. Examples of oil-soluble antioxidants include BHT (butylated hydroxytoluene), BHA (butylated hydroxyanisole), tocopherol (vitamin E), tocopheryl acetate, ascorbyl palmitate, hydroquinone, di-t-butylhydroquinone, propyl gallate, and the like. If desired, a water-soluble antioxidant may be used in the aqueous phase (especially sodium metabisulfite), and an oil-soluble antioxidant in the organic phase. Other optional ingredients in the formulation include chelating agents such as EDTA (ethylenediaminetetraacetic acid) and its salts, for example disodium EDTA, trisodium NTA, etidronic acid and its salts, sodium dihydroxyethylglycinate, citric acid and its salts, and the like. Suitable preservatives include the parabens, such as methylparaben, propylparaben, isopropylparaben, butylparaben, and isobutylparaben, and their salts such as sodium butylparaben, benzoic acid and its salts and esters, benzyl alcohol, urea derivatives such as diazolidinyl urea, imidazolidinyl urea, and DMDM hydantoin, sorbic acid and its salts, and the like. Suitable colorants and fragrances will be a matter of choice, provided only that they should be compatible with the formulation and the dispensing container.

The oil-in-water emulsion may be prepared by methods well known to the art, typically by mixing the aqueous phase ingredients and a dispersant with heating until a uniform solution or dispersion is obtained (optionally in several stages), adding the free fluorouracil content, mixing the organic phase ingredients with heating until a uniform solution or dispersion is obtained (also optionally in several stages), then adding the organic phase to the aqueous phase with agitation (e.g. stirring or other shearing technique) to form an oil-in-water emulsion of the two phases. These and all other processing steps may be performed under an inert atmosphere, for example of nitrogen. The emulsion is cooled with stirring. Once the emulsion is sufficiently cooled, it may be homogenized if necessary. The fluorouracil-impregnated porous microparticles may be added once the emulsion is first formed, or during or after cooling; and temperature-sensitive or volatile ingredients, such as any fragrance, are added and uniformly dispersed in the emulsion after cooling. The emulsion may be degassed, if necessary or desired. Finally, storage or dispensing containers are filled with the formulation.

Suitable creams for this invention are semi-solid oil-in-water emulsions and are generally higher in oil content. They are typified by a relatively heavy consistency. Creams are attractive in that a small amount can be used to cover a comparatively large surface area. Furthermore, creams are easily applied but not easily washed off and, thus, are frequently employed as treatment and protective products. Creams of a heavier variety are formulated for more intensive moisturizing. Such creams are characterized by augmented levels of absorbent and humectant materials.

Creams can be prepared by methods well known in the art (*Chemistry and Technology of the Cosmetics and Toiletries Industry,* 2nd edition, Blackie Academic & Professional (Chapman & Hall), 1996, ch. 1 and 3). They are usually sold in tubes or jars.

Suitable lotions for this invention are oil-in-water emulsions typically containing about 10–15% oil phase and about 85–90% water phase—a higher water phase content than that found in creams. Lotions are attractive formulations in that they flow easily and rub in quickly without leaving behind a feeling of stickiness. They thus provide the ability to hydrate dry skin quickly.

Lotions can be prepared by methods well known in the art (*Chemistry and Technology of the Cosmetics and Toiletries Industry,* 2nd edition, Blackie Academic & Professional (Chapman & Hall), 1996, ch. 1 and 3). Lotions are typically sold in tubes and bottles.

Dispensing Containers

The term "dispensing container" refers to a container suitable for containing the formulations of the first aspect of this invention. Dispensing containers are well known in the packaging art; and suitable containers include jars, tubes (of the kind widely used to hold topical formulations, cosmetics, and the like), pumps, sachets or pouches, and the like.

The dispensing containers are fillable and closable/sealable by methods well known to the packaging art; for example, already capped or sealed and capped tubes open at the bottom end are filled from the open end and sealed by any suitable means, typically by heat sealing (heating either by direct conduction, applicable to all materials, or by inductive heating, applicable if a metal foil or foil laminate is present in the area of the container to be sealed).

Particularly convenient multi-dose dispensing containers are tubes; and particularly convenient single-dose dispensing containers are sachets or pouches formed from a foil laminate, as these containers are already widely used as single-dose or sample containers for topical medications or cosmetics and may be conveniently filled with the formulation and sealed by automated packaging machinery.

The invention is illustrated by the following non-limiting Examples.

EXAMPLE 1.

Fluorouracil-impregnated Microparticles, 15%.

Fluorouracil-impregnated microparticles were prepared to the following formulation:

| Ingredient | Weight percent |
|---|---|
| Fluorouracil | 15.0 |
| Dimethicone 200, 350 cst | 40.0 |
| Microparticles[1] | 45.0 |

[1]The microparticles used were Microsponge ® (Advanced Polymer Systems, Inc.), porous methyl methacrylate/ethylene glycol dimethacrylate crosspolymer microparticles, having a weight average particle diameter of 20 μm, a surface area of 225 m$^2$/g, and a pore volume of 1 cm$^3$/g.

The microparticles were added to a blender and warmed. Sterile water, 3.5 g per gram microparticles, was added to a mix tank and warmed. One-third of the fluorouracil was added, and the mixture was heated to and mixed until the fluorouracil had dissolved. The solution was added to the blender and mixed until absorbed into the microparticles; and the microparticles were then dried under vacuum to remove the water. This process was repeated twice more to produce the fluorouracil-impregnated microparticles as an intermediate product, which may be isolated and used directly, if desired. Dimethicone was added to the intermediate product and mixed in until fully entrapped. The fully-impregnated microparticles as the final product were discharged and packaged into approved containers.

EXAMPLE 2.

Oil-in-water Emulsion Formulation Containing Fluorouracil, 1.5%, and Fluorouracil Impregnated in Porous Microparticles, 3.5%

An oil-in-water formulation of the invention was prepared with the following ingredients:

| Ingredient | Weight percent |
|---|---|
| Part I | |
| Purified water, USP | 27.67 |
| Carbomer 940, NF (Carbopol 940) | 0.40 |
| Part II | |
| Glycerin, USP (Emery 912) | 7.00 |
| PEG-8 (Carbowax-400) | 10.00 |
| Part III | |
| Fluorouracil, USP | 1.50 |
| Part IV | |
| Polysorbate 80 (Tween 80) | 4.50 |
| Sorbitan oleate (Span 80) | 3.50 |
| Octyl hydroxy stearate (Wickenol-171) | 12.00 |
| Methyl gluceth-20 (Glucam E-20) | 5.00 |
| Stearic acid, NF (Emersol 132 Triple press) | 1.50 |
| Part V | |
| Fluorouracil, USP (15% in microparticles with dimethicone, from Example 1) | 23.33 |
| Part VI | |
| Triethanolamine, 99% | 0.40 |
| Purified water, USP | 1.00 |
| Part VII | |
| Propylene glycol, diazolidinyl urea, methylparaben, and propylparaben blend (Germaben II) | 1.20 |
| Purified water, USP | 1.00 |

The water of Part I was weighed in a suitable container and the carbomer 940 added and mixed for about 30 minutes, then transferred to a mixing vessel. The ingredients of Part II were added to the mixture, and the mixture heated to 75–80° C. The free fluorouracil of Part III was then carefully added to the mixture with good mixing for 5–10 minutes, forming the aqueous phase. The ingredients of Part IV were mixed and heated to 75–80° C., forming the oil phase. The oil phase was slowly added to the aqueous phase under increased mixing, forming an oil-in-water emulsion, and the heating terminated. Part V was added very carefully to the mixture of Parts I through IV under mixing, until complete dispersion was achieved. The ingredients of Part VI were pre-mixed and added with mixing, and the temperature lowered. At 40° C., the ingredients of Part VII were pre-mixed and added to the mixture, and the temperature was lowered further to 30° C. or below. The formulation was packaged in high-density polyethylene tubes.

EXAMPLE 3.

Oil-in-water Emulsion Formulation Containing Fluorouracil, 0.15%, and Fluorouracil Impregnated in Porous Microparticles, 0.35%, with Dimethicone, 8.5%.

A formulation similar to that of Example 2, but using 0.15% free fluorouracil, 2.33% fluorouracil in porous microparticles (15% in microparticles with dimethicone, from Example 1), and 21% dimethicone in porous microparticles (40% in microparticles), gave a formulation similar in physical characteristics to that of Example 2 but containing one-tenth the fluorouracil content of the formulation of Example 2 and containing 8.5% dimethicone.

These and similar formulations displayed stability and retained potency for at least six months at 40° C. and at least twelve months at 30° C. Their stability was essentially unchanged by five consecutive freeze-thaw cycles.

While this invention has been described in conjunction with specific embodiments and examples, it will be apparent to a person of ordinary skill in the art, having regard to this disclosure, that equivalents of the specifically disclosed materials and techniques will also be applicable to this invention; and such equivalents are intended to be included within the following claims.

What is claimed is:

1. A topical formulation containing fluorouracil, comprising:
   (i) an oil-in-water emulsion; and
   (ii) dispersed within the oil-in-water emulsion,
      (a) fluorouracil; and
      (b) fluorouracil-impregnated porous microparticles,
   where the formulation has a total fluorouracil content that the sum of the fluorouracil in (ii)(a) and the fluorouracil in the fluorouracil-impregnated porous microparticles of (ii)(b) of from about 0.01% to about 10% by weight and a free fluorouracil content that is the fluorouracil in (ii)(a) of from 20% to 50% by weight of the total fluorouracil content.

2. The formulation of claim 1, where the formulation has a total fluorouracil content of from about 0.1% to about 5% weight.

3. The formulation of claim 2, where the formulation has a total fluorouracil content of 0.5% by weight.

4. The formulation of claim 1, where the formulation has a free fluorouracil content of 30% by weight of the total fluorouracil content.

5. The formulation of claim 1, where the formulation has a total fluorouracil content of 0.5% by weight and a free fluorouracil content of 30% by weight of the total fluorouracil content.

6. The formulation of claim 1, where the porous microparticles have a weight average diameter less than 50 μm.

7. The formulation of claim 6, where the porous microparticles have a weight average diameter of about 20 μm.

8. The formulation of claim 1, where the porous microparticles comprise a cross-linked polymer selected from the group consisting of a styrene/divinylbenzene crosspolymer, a vinyl stearate/divinylbenzene crosspolymer, a methyl methacrylate/ethylene glycol dimethacrylate crosspolymer, and a lauryl methacrylate/ethylene glycol dimethacrylate crosspolymer.

9. The formulation of claim 8, where the porous microparticles comprise a methyl methacrylate/ethylene glycol dimethacrylate crosspolymer.

10. The formulation of claim 1, further comprising at least one additional component selected from an antioxidant, a chelating agent, a colorant, a fragrance, and a preservative.

11. The formulation of claim 1, where the formulation has a total fluorouracil content of 0.50%, a free fluorouracil content of 30% by weight of the total fluorouracil content, and the porous microparticles have a weight average diameter of about 20 μm and comprise a methyl methacrylate/ethylene glycol dimethacrylate crosspolymer.

12. A method for the topical application of fluorouracil, comprising topical administration of the formulation of claim 1.

13. A method for the topical application of fluorouracil, comprising topical administration of the formulation of claim 2.

14. A method for the topical application of fluorouracil, comprising topical administration of the formulation of claim 3.

15. A method for the topical application of fluorouracil, comprising topical administration of the formulation of claim 4.

16. A method for the topical application of fluorouracil, comprising topical administration of the formulation of claim 5.

17. A method for the topical application of fluorouracil, comprising topical administration of the formulation of claim 11.

18. A method of treating an animal having a disease capable of treatment by topical administration of fluorouracil, comprising topically administering to that animal a therapeutically effective amount of the formulation of claim 1.

19. A method of treating an animal having a disease selected from solar keratosis, actinic keratosis, and superficial basal cell carcinoma, comprising topically administering to that animal a therapeutically effective amount of the formulation of claim 1.

20. A method of treating an animal having a disease selected from solar keratosis, actinic keratosis, and superficial basal cell carcinoma, comprising topically administering to that animal a therapeutically effective amount of the formulation of claim 11.

* * * * *